United States Patent
McVicker et al.

(10) Patent No.: US 6,245,577 B1
(45) Date of Patent: Jun. 12, 2001

(54) IGG ANTIBODY TESTING METHOD

(75) Inventors: Jerry K. McVicker; Glenda C. Rouse, both of Boone, IA (US); Denny M. Barrantes, Scarborough, ME (US)

(73) Assignee: Midland Bioproducts Corporation, Boone, IA (US)

(*) Notice: Subject to any disclaimer, the term of this patent is extended or adjusted under 35 U.S.C. 154(b) by 0 days.

(21) Appl. No.: 09/152,171

(22) Filed: Sep. 11, 1998

(51) Int. Cl.[7] .................................................. G01N 33/543
(52) U.S. Cl. .............................. 436/518; 422/55; 422/56; 422/57; 435/970; 435/805; 435/810; 436/513; 436/514; 436/524; 436/530; 436/169; 436/805; 436/810
(58) Field of Search ..................................... 436/513, 514, 436/518, 524, 530, 169, 805, 810; 435/970, 805, 810; 422/55–58

(56) References Cited

U.S. PATENT DOCUMENTS

| | | | |
|---|---|---|---|
| 4,943,522 | * 7/1990 | Eisinger et al. ...................... | 435/805 |
| 5,384,264 | * 1/1995 | Chen et al. ........................... | 436/525 |
| 5,559,041 | * 9/1996 | Kang et al. ........................... | 436/529 |
| 5,602,040 | * 2/1997 | May et al. ............................. | 436/514 |
| 5,656,503 | 8/1997 | May et al. . | |
| 5,798,273 | 8/1998 | Shuler et al. . | |

OTHER PUBLICATIONS

Thomas E. Besser, DVM.Phd, & Clive C. Gay, DVM. MVSc, FACVS; The Importance of Colostrum to the Health of the Neonatal Calf; Mar. 1994; vol. 10–No. 1, pp. 107–117; Washington State University College of Veterinary Medicine, Pullman, Washington.

T. E. Besser and C.C. Gay; Colostral Transfer of immunoglobulins to the Calf; Vet Manual Vol. 33 1993—pp. 53–61.

F. B. Garry, DVM,MS; R. Adams, MA, DVM; M. B. Cattell,DVM.MS; R.P. Dinsmore, DVM, MS; Comparison of Passive Immunoglobulin Transfer to Dairy Calves Fed Colostrum of Commercially Available Colostral–Supplement Products; Jan. 1, 1996; JAVMA, vol.208, No. 1, pp. 107–110.

Franklyn Garry, DVM, MS; Brain Aldridge, BVSc and Ragan Adams, MA, DVM; Role of Colostral Transfer in Neonatal Calf Management: Current Concepts in Diagnosis; Aug. 1993; vol. 15, No. 8, pp.1167–1175; Coloradao State University.

D. G. White, MA, VetMB, PhD, MRCVS; Colostral Supplementation in Ruminants; Feb. 1993; vol. 15, No. 2, pp. 335–342; The Royal Veterinary College University of London.

(List continued on next page.)

Primary Examiner—Christopher L. Chin
(74) Attorney, Agent, or Firm—Henderson & Sturm LLP

(57) ABSTRACT

A method of determining the concentration of IgG antibodies in the biological fluids of mammals. The assay may be performed in a lateral flow cassette or dipstick format where dehydrated immobilized reagents are spaced along a membrane. A sample of a mammalian biological fluid is exposed first to an IgG complexing agent to yield a conjugate. The conjugate then moves along the membrane and is exposed to a standard mammalian IgG applied to the membrane at a test position. Binding of the IgG is indicated by a color change at the test position on the membrane. A control reagent of dehydrated anti-IgG complexing agent may be applied to the membrane at the control position spaced downstream from the test position. Interaction of the IgG complexing agent with the anti-IgG complexing agent forms a visible line at the control position on the membrane.

8 Claims, 2 Drawing Sheets

TOP VIEW

S: Colloidal Gold Labelled Protein A
T: Bovine IgG
C: Anti-Protein A

CROSS SECTION

OTHER PUBLICATIONS

S. F. Abel Francisco, MS, and J. D. Quigley III, Phd; Serum Immunoglobulin Concentrations After Feeding Maternal Colostrum of Maternal Colostrum Plus Colostral Supplement to Diary Calves; Jul. 1993; Am J Vet Res, vol. 54, No. 7, pp. 1051–1054; University of Tennessee.

Gerald H. Stott; Immunoglobulin Absorption in Calf neonates with Special Considerations of Stress; 1980; pp. 681–688; University of Arizona, Tucson.

D. P. Olson, C. J. Papasian and R. C. Ritter; The Effects of Cold Stress on Neonatal Calves; Jan. 1980; pp. 19–23; University of Idaho.

Thomas E. Besser, DVM, Phd; Clive C. Gay, DVM, MVSc; and Lori Pritchett, BS; Comparison of Three Methods of Feeding Colosturm to Dairy Calves; Feb. 1, 1991; JAVMA, vol. 198, No. 3, pp. 419422; Washington State University, Pullman, Washington.

D. G. White and A. H. Andrews; Adequate Concentration of Circulating Colostral Proteins for Market Calves; Aug. 2, 1986; pp. 112–114; Royal Veterinary College.

Sheikh A. Selim, DVM, Msc, MPVm, et al.; Serum Immunoglobulins in Calves: Their Effects and Two Easy, Reliable Means of Measurement; Apr. 1995; Veterinary Medicine Apr. 1995.

John E. Butler; Bovine Immunoglobulins: A Review; Journal of Dairy Science vol. 52, No. 12, pp. 1895–1909; U.S. Department of Agriculture, Washington, D.C.

J. P. Mach, J. J. Pahud and H. Isliker; IgA With "Secretory Piece" in Bovine Colostrum and Saliva; Nature vol. 223, Aug. 30, 1969 952–954.

D. K. Hammer, B. Kickhofen and T. Schmid; Detection of Homocytotropic Antibody Associated With a Unique Immunoglobulin Class in the Bovine Species; 1971; pp. 249–257; Eur. J. Immunol.

K. Nielsen, W. Holmes, B. Wilkie and I. Tizard; Bovine Reaginic Antibody; 1976; 441–440; Int. Archs Allergy appl. Immun. 51; Ontario Veterinary college, University of Guelph, Guelph, Ont.

C. L. Babel and R. W. Lang; Identification of a New Immunoglobulin Sublcass in Three Ruminant Species; Immunochemistry, p. 272, No. 368.

B. I. Osburn; The Ontogeny of the Ruminant Immune System and Its Significance in the Understanding of Maternal–Fetal–Neonatal Relationships; pp. 91–103; University of California.

L. R. Etzel, BS; R. E. Strohbehn, MS; and J. K. McVicker, MS; Development of an Automated Trubidimetric Immunoassay for Quantification of Bovine Serum Immunoglobulin G; Nov. 1997; AJVR, vol. 58, No. 11, pp. 1201–1205; AMPC, Inc., Ames, Iowa.

E. Bogin, Y. Advidar, s.Shenkler, Bat–Ami Israeli, N. Spiegel and R. Cohen; A Rapid Field Test for the Determination of Colostral Ingestion by Calves, Based on γ–Blutamyltransferase; 1993; Eur. J. Clin. Chem. Clin. Biochem. vol. 31, pp. 695–699.

Peter Nansen; Selective Immunoglobulin Deficiency in Cattle and Susceptibility to Infection; 1972; pp. 49–54; Royal Veterinary and Agricultural University.

P. W. Wells and P. Eyre; Bovine Homocytotropic (Skin–Sensitizing) Antibody; 1972; pp. 105111; Department of Veterinary Pathology.

Clive C. Gay; Failure of Passive Transfer of Colostral Immunoglobulins and Neonatal Disease in Calves: A Review; pp. 346–364; Washington State University.

* cited by examiner

TOP VIEW

S: Colloidal Gold Labelled Protein A
T: Bovine IgG
C: Anti-Protein A

TOP VIEW

S: Colloidal Gold Labelled Protein A
T: Bovine IgG
C: Anti-Protein A

TOP VIEW

S: Colloidal Gold Labelled Goat Anti-Bovine IgG
T: Bovine IgG
C: Anti-Goat IgG

CROSS SECTION

TOP VIEW $T_1$ = Bovine IgG at 5 mg/ml
$T_2$ = Bovine IgG at 10 mg/ml
$T_3$ = Bovine IgG at 15 mg/ml S: Colloidal Gold Labelled Protein A
T: Bovine IgG
C: Anti-Protein A

IGG ANTIBODY TESTING METHOD

CROSS-REFERENCE TO RELATED APPLICATIONS

Not Applicable.

STATEMENT REGARDING FEDERALLY SPONSORED RESEARCH OR DEVELOPMENT

Not Applicable.

AUTHORIZATION PURSUANT TO 37 C.F.R. §1.71 (d) (e)

A portion of the disclosure of this patent document, including appendices, may contain material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates generally to immunoglobulin testing methods and more particularly to a method of determining the concentration of IgG antibodies in biological fluids of mammals.

2. Description of the Related Art

The numbers in brackets refer to the publications listed in the Appendix, the teachings of which are incorporated herein by reference.

The bovine immunoglobulin system closely resembles that of other species with respect to physiochemical properties and nomenclature. Well characterized classes include IgG, IgM [13],IgA [14] and IgE [15–17]. The IgG class contains two documented subclasses, IgG1 and IgG2, which have antigenic differences in the Fc portion of the heavy chain. A possible third subclass, IgG3, has been reported [18], but remains unconfirmed. It is presumed that additional heterogeneity awaits discovery.

In cattle, the newborn calves are virtually devoid of any detectable levels of immunoglobulin [19, 20]. This is due to a syndesmochorial type placental attachment, which restricts the transfer of maternal immunoglobulins to fetal blood. Essentially, the neonatal calf relies entirely on passive immunity for it's immune protection during the first weeks of life. This transfer of IgG is important in reducing mortality in calves [1, 2, 4]. Stress from birthing, temperature, or herd management practices are factors that may adversely affect the passive transfer of IgG [7–8].

Frequently, colostral supplements are included in calf rations to ensure that adequate amounts of IgG are provided [3, 5, 6]. These supplements include either frozen or natural colostrum, and/or commercial supplements. Although feeding fresh or stored colostrum seems simple, obtaining and storing adequate amounts of quality colostrum is often difficult and laborious. Additionally, the high cost of commercial colostrum prohibits its use on a routine basis. From a herd management aspect, there would be a tremendous time and monetary savings if only those animals in need of the colostral supplement could be identified quickly and accurately.

In order to assess the passive transfer of maternal immunoglobulin, serum IgG concentrations of neonatal calves may be measured. Historically, the measurement of bovine serum IgG has been performed by several methods. These methods can be divided into three main groups [21]:

a.) Accurate tests for immunoglobulin, which may or may not provide a rapid result. For these methods, blood samples must be shipped to, and analyzed in the laboratory and require professional training and equipment [12,20].

b.) Tests which can be done in a relatively short time on the farm and under "field" conditions, and do not require much training or equipment. These tests however are qualitative in nature and are not accurate. This group includes the glutaraldehyde test, the zinc sulfate turbidity test and the determination of total protein by refractometry.

c.) Tests based upon proteins other than IgG. This includes testing for γ-glutamyltransferase, a serum enzyme whose concentration has been reported to correlate with total globulin levels [21]. This method has never been well accepted.

It is generally recommended that calves receive a minimal dose of 100 g of immunoglobulin at birth [9,10]. Calf serum IgG concentrations greater than or equal to 10 mg/ml indicates adequate passive transfer [10,11]. Values less than 10 mg/ml are considered to be indicative of Failure of Passive Transfer (FPT). It is widely accepted that the treatment for FPT is to administer two feedings of colostrum (50 g IgG/L), one within the first 24 hours of birth and the second 12 hours later. Treatment at times outside this window tend to be less effective due to the decrease in permeability of the calf intestine to ingested antibodies.

Those concerned with these and other problems recognize the need for fast, accurate and simple assay for IgG.

BRIEF SUMMARY OF THE INVENTION

The present invention provides a method of determining the concentration of IgG antibodies in the biological fluids of mammals. The assay may be performed in a lateral flow cassette or dipstick format where dehydrated immobilized reagents are spaced along a membrane. A sample of a mammalian biological fluid is exposed first to an IgG complexing agent to yield a conjugate. The conjugate then moves along the membrane and is exposed to a standard mammalian IgG applied to the membrane at a test position. Binding of the IgG is indicated by a color change at the test position on the membrane. A control reagent of dehydrated anti-IgG complexing agent may be applied to the membrane at the control position spaced downstream from the test position. Interaction of the IgG complexing agent with the anti-IgG complexing agent forms a visible line at the control position on the membrane.

Therefore, an object of the present invention is the provision of an improved IgG antibody testing method.

BRIEF DESCRIPTION OF THE SEVERAL VIEWS OF THE DRAWINGS

Other objects, advantages, and novel features of the present invention will become apparent from the following detailed description of the invention when considered in conjunction with the accompanying drawings, wherein.

DETAILED DESCRIPTION OF THE INVENTION

The following examples are all illustrations of the best mode of carrying out the invention. They are obviously not to be construed as limitative of the invention since various other embodiments can readily be involved in view of the teachings provided herein.

EXAMPLE 1

The following Example discloses a dry chemistry, lateral flow immunoassay aimed at determining if calf serum, plasma, or whole blood contains IgG concentrations above or below 10 mg/ml. This assay provides the advantages of speed, accuracy and simplicity. A convenient kit is provided so that the user can easily conduct the assay under field conditions.

Kit Contents

The kit will consist of the following:

1.) One lateral flow cassette enclosed in a foil wrapper with desiccant;
2.) One disposable Pasteur pipette with a 200 µl draw volume; and
3.) One vial of dilution buffer.

Materials

Figure 1:
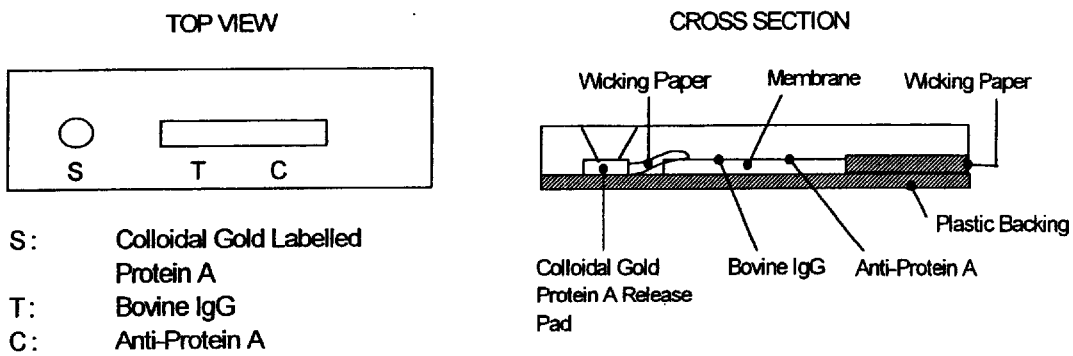
FIG. 1 is a schematic illustration of the method of the present invention in a lateral flow cassette format.

The lateral flow cassette is manufactured using the following materials in the manner illustrated in FIG. 1:

1.) Lateral Flow Plastic Housing: Schleicher & Schuell or equivalent;
2.) Plastic Backing-polyester, 100–400 µm thick: Schleicher & Schuell or equivalent;
3.) Supported Membrane: Schleicher & Schuell or equivalent Nitrocellulose, Grade AE100, Capillary Rise Rating 90–120 sec, 4 cm dIH$_2$O;
4.) Blocking Agent: 1% Fish Gelatin in Dilution Buffer: Sigma or equivalent;
5.) Protein A Release Pad: Schleicher & Schuell or equivalent Borosilicate Glass, Basis Weight 64 g/m$^2$ or Non-Woven Rayon, Basis Weight 70 g/m$^2$ could be used interchangably;
6.) Wicking Paper: Schleicher & Schuell or equivalent Cotton Linter paper, Basis Weight 165 g/m$^2$;
7.) Colloidal Gold Labeled Protein A: Arista Biologicals or equivalent Protein A Colloidal Gold, particle size range 10 to 65 nm, 10–12 OD units at 540 nm;
8.) Bovine IgG Standard: Midland BioProducts Corp. or equivalent Greater than 98.5% purity, 19.2 mg/ml; and
9.) Chicken Anti-Protein A: Arista Biological or equivalent Affinity Purified at 1 mg/ml.

The remaining components of the kit include:

10.) Pasteur Pipette (200 µl): Samco or equivalent;
11.) Dilution Buffer: 0.05M Tris, 0.3 M NaCl, 0.005 M EDTA, 0.1% NaN$_3$, pH 7.4 (Sigma or equivalent);
12.) Dilution Vial: Wheaton or equivalent Sampule®, 7 ml capacity, cat. #986644; and
13.) Desiccant: Multisorb Technologies or equivalent.

Preparation of Bovine IgG Standard

Improper standardization during assay development is a common downfall to many clinical assays. One of the most common errors associated with standardization is the incorrect assignment of the standard's concentration. In order to develop a dependable test, it is important to use only an extremely pure standard. By using a pure standard, the concentration could reliably be determined. Because Applicants were unable to obtain commercially available bovine IgG at the required purity, they prepared the material.

The preparation of the standard was begun with a pool of normal bovine serum (Bayer Corp. Cat #83-201). Protein G affinity chromatography was used to isolate the IgG at a purity of approximately 85%. In order to remove the residual 15% of non-IgG proteins, size exclusion and immunoaffinity chromatography matrices were employed. Determination of the IgG purity was accomplished by: i.) immunoelectrophoresis, ii.) counter-immunoelectrophoresis, and iii.) SDS-PAGE electrophoresis[20].

Methods

The format that was developed to detect bovine IgG antibodies involves a dry chemistry principle (dehydrated and immobilized reagents). A small volume of biological fluid (including but not limited to whole blood, plasma, serum, colostrum, urine) is obtained from the calf. Using the 200 µl pipette, the sample is drawn up then mixed with the buffer diluent using pipette action. Using the same pipette, a portion of the diluted sample is transferred to the lateral flow cassette and applied at the S (sample) position. The addition of the diluted sample rehydrates the colloidal gold labeled Protein A in the release pad. This allows bovine IgG, if present, to bind to the colloidal gold labeled Protein A.

The concentrations of the test reagents are as follows:

Control line "C"; Chicken anti-protein A, 0.3 mg/ml sprayed at 1 µl/cm;

Test line "T"; Bovine IgG, 4.0 mg/ml sprayed at 1 µl/cm; and

Protein A Colloidal Gold; OD 50 sprayed at 2 µl/cm.

If the bovine IgG concentration is greater than 10 mg/ml, a complex will form with the colloidal gold labeled Protein A. The complex will move down the membrane but it will not be able to bind to the immobilized bovine IgG since the Protein A binding sites are already occupied. The complex will, however, interact with the immobilized anti-Protein A and cause the formation of a visible pink line at the C position. (FIG. 1).

If the bovine IgG concentration is less than 10 mg/ml, no complex will form with the colloidal gold labeled Protein A. The colloidal gold labeled Protein A will move down the membrane and bind with the immobilized bovine IgG causing a visible pink line to form at the T (test) position. Residual colloidal gold labeled Protein A will interact with the immobilized anti-Protein A and cause the formation of a second visible pink line at the C (control) position (FIG. 1).

The method using the lateral flow cassette illustrated in FIG. 1 can be summarized as follows:

1.) Sample is diluted ⅕s with Diluent.
2.) Diluted sample is applied to well (approx. 200 µl).

If Bovine IgG>10 mg/ml

3.) Bovine IgG in diluted sample complexes with gold labeled protein A.
4.) The complex will move down the membrane but will not bind to the immobilized bovine IgG (T) due to the fact it is already bound to bovine IgG in the diluted sample.
5.) Once the complex and the anti-protein A interact, the affinity prohibits any further movement and a visible line forms at the "C" position.

If Bovine IgG>10 mg/ml
- 3.) The lack of bovine IgG in the diluted sample causes the excess colloidal gold labeled protein a to migrate up the membrane.
- 4.) The excessive amount of colloidal gold labeled protein A reacts with both the immobilized bovine IgG and the anti-protein A on the membrane.
- 5.) The affinity causes the colloidal gold labeled protein A to stop moving with the buffer and two lines form at the "T" and "C" positions.

EXAMPLE 2

The following alternative designs are among those that could be used without departing from the novel teachings of the present invention.

Alternate 1

The test could be applied to other mammals as well (including but not limited to humans, horses, pigs, dogs, cats). The only changes that would be required would be the composition and concentration of the standard. For instance, if it were to be used with horses, the standard would be a horse IgG at a clinically significant concentration. The reason that the test could be modified so easily is that Protein A binds effectively to IgG from all mammals tested to date.

Alternate 2

The test could incorporate Protein G rather than Protein A. Protein G and Protein A have very similar binding characteristics and are often used interchangeably. The test could also use a mixture of Protein A and Protein G which is also commercially available.

Alternate 3

The test could use native or recombinant forms of the Protein G or Protein A. These are frequently used interchangeably.

Alternate 4

Cosmetic changes to the test:

Color of the lines

Color of the background

Shape of the lines

Shape of the background

Shape of the cassette

More than one test per cassette

Transposition of the control and test lines

Elimination of the control line

Alternate 5

The nitrocellulose membrane could be changed to any membrane filter with adequate protein binding capacities (e.g. polyvinylidene difluoride, mixed cellulose ester). Currently, the test requires a minimum of 20 $\mu g/cm^2$ protein binding capacity. In addition the membrane could be changed to a different porosity in order to increase the capillary flow of the sample. The device of Example 1 currently requires a capillary rise of not more than 210 sec, 4 cm d$IH_2O$. The lower the capillary rise value, the faster the flow of the sample and hence the quicker the results of the test can be determined.

Alternate 6

The chicken anti-Protein A antibody could be produced in any animal species, not specifically chicken. In the future it is anticipated that the anti-Protein A protein could be produced in plant tissue (including but not limited to soybeans, corn, etc.).

Alternate 7

The Pasteur pipette could be of any volume that would produce a dilution range of between 1/24 and 1/26 when teamed with the dilution buffer. For instance, if 50 $\mu l$ pipette was used, the dilution buffer could be changed to 1.15 ml or 1.25 ml.

Alternate 8

The dilution buffer could consist of any buffer within the pH 6–8 range with an ionic strength of at least 13 mS/cm. Shelf life can be extended by the addition of preservatives including but not limited to sodium azide and thimerosal.

Alternate 9

The test could be edited so that no dilution of the serum sample would have to be made. This would require a change in all the concentrations of the reagents (colloidal gold Protein A, bovine IgG standard, and anti-Protein A). The changes would likely be increases in concentrations.

Alternate 10

The test could be edited so that a filter was included that would remove any blood cells or particulate matter (PlasmaSep, Whatman). In the event that the test was changed so that no dilution of the sample was required, then this type of a filter would be required. Without a dilution, the residual blood cells would cause such an increase in background membrane staining, that it would render the test nearly impossible to read with the naked eye.

Alternate 11

The Protein A could be coupled to latex particles rather than the colloidal gold. Since the purpose of the colloidal gold is to provide a visualization of the reaction between the protein A, sample, standard and anti-Protein A, any latex particle that would allow visualization could be used. The latex particle would need to be of a size that would facilitate movement through the membrane (10–65 nm).

Alternate 12

The test could easily be adapted to a dipstick format (FIG. 2) rather than a lateral flow assay (FIG. 1). The change would require only two additional pieces of protective covering. This method would eliminate the need for the cassette. Rather than applying the sample into the well formed by the cassette, the colloidal gold Protein A end of the dipstick would be briefly immersed in the sample.

Figure 2:
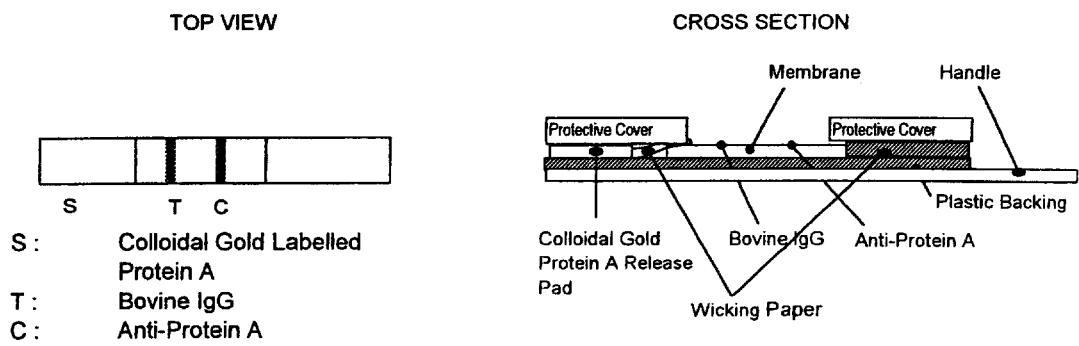
FIG. 2. is a schematic illustration of the method in a dipstick format.

The method using the dipstick format illustrated in FIG. 2 can be summarized as follows:

1.) Sample is diluted 1/25 Diluent.

2.) Colloidal gold Protein A end of the dipstick apparatus is immersed in diluted sample.

If Bovine IgG>10 mg/ml
- 3.) Bovine IgG in diluted sample complexes with gold labeled protein A.
- 4.) The complex will move up the membrane but will not bind to the immobilized bovine IgG (T) due to the fact it is already bound to bovine IgG in the diluted sample.
- 5.) Once the complex and the anti-protein A interact, the affinity prohibits any further movement and a visible line forms at the "C" position.

If Bovine IgG>10 mg/ml
- 3.) The lack of bovine IgG in the diluted sample causes the excess colloidal gold labeled protein A to migrate up the membrane.
- 4.) The excessive amount of colloidal gold labeled protein A reacts with both the immobilized bovine IgG and the anti-protein A on the membrane.
- 5.) The affinity causes the colloidal gold labeled protein A to stop moving with the buffer and two lines form at the "T" and "C" positions.

Alternate 13

Rather than colloidal gold or latex-labeled Protein A, a monoclonal or polyclonal anti-bovine IgG antibody could be used (labeled with either colloidal gold or latex). The anti-bovine IgG antibody would bind the IgG just like the Protein A. By binding to the IgG, a complex could form but rather than a Protein A/bovine IgG complex, it would be an anti-bovine IgG/bovine IgG complex. If an antibody were used, the anti-Protein A would have to be changed to an antibody directed against the IgG of whatever species was used to produce the anti-bovine IgG.

Figure 3:
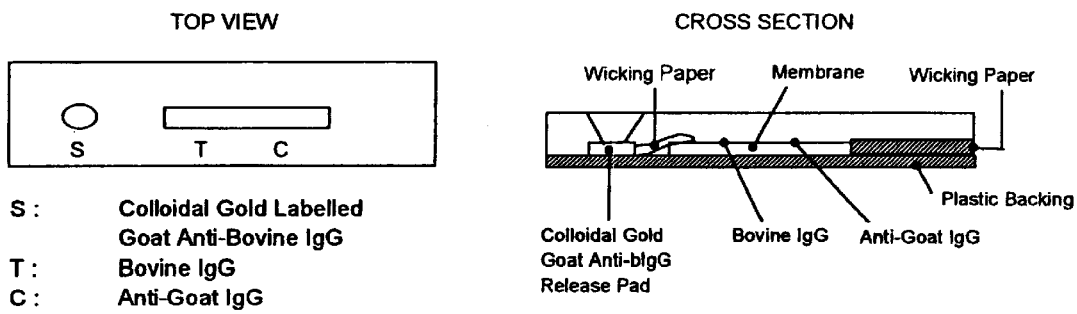
FIG. 3 is a schematic illustration similar to FIG. 1, but illustrating use of different reagents.

As illustrated in FIG. 3, if a colloidal gold labeled goat anti-bovine IgG is used in the release pad to form the complex, then the antibody at the C (control) position would be anti-goat IgG. The T (test) line would remain bovine IgG.

Alternate 14

The detection limits could be changed so that the test read positive at some other clinically relevant concentration. Currently, the limit has been set at 10 mg/ml, but this could be changed.

Alternate 15

Figure 4:
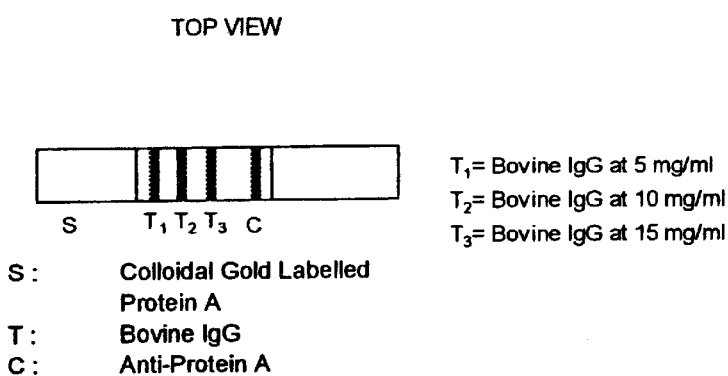
FIG. 4 is a schematic illustration of a membrane having multiple test positions to indicate varying concentration levels of IgG antibodies in the tested sample.

The test could also include multiple test lines aimed at detecting several concentrations of IgG in the sample. For instance there may be a graded assay in which values from 5–15 mg/ml are observed as multiple lines as illustrated in FIG. 4.

Alternate 16

The bovine IgG used on the test line could be changed to another animal immunoglobulin (IgG). The only considerations would be that the IgG interact with the complexing agent and that it was determined to be of comparable purity to the bovine IgG used in Example 1.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

APPENDIX

1. Besser T E, Gay C G. The importance of colostrum to the health of the neonatal claf. *Vet Clin North Am Food Anim Pract* 1994; 1:107–117.
2. Besser T E, Gay C G. Colostral transfer of immunoglobulins to the calf. *Vet Annu* 1993;33:53–61.
3. Garry F, Adams R, Cattell M B, et al. Comparison of passive immunoglobulin transfer to dairy calves fed colostrum or commercially available colostral-supplement products. *J Am Vet Med Assoc* 1996;208:107–110.
4. Garry F, Aldridge B, Adams R. Role of colostral transfer in neonatal calf management: current concepts in diagnosis. *Compend Contin Educ Prat Vet* 1993;15:1167–1175.
5. White D G. Colostral supplementation in ruminants. *Compend Contin Educ Prat Vet* 1993;15:335–342.
6. Abel Francisco S F, Quigley J D. Serum immunoglobulin concentrations after feeding maternal colostrum or maternal colostrum plus supplement to dairy calves. *Am J Vet Res* 1993;54:1051–1054.
7. Scott G H. Immunoglobulin adsorption in calf neonates with special considerations of stress. *J Diary Sci* 1980;63:681–688.
8. Olson D P, Papasian C J, Ritter R C. The effects of cold stress on neonatal calves II. Adsorption of colostral immunoglobulins. *Can J Comp Med* 1980;44:19–23.
9. Besser T E, Gay C C, Protchett L. Comparison of three methods of feeding colostrum to dairy calves. *J Am Vet Med Assoc* 1991;198:419–422.
10. Gay C C. Failure of passive transfer of colostral immunoglobulins and neonatal disease in calves: a review, in Proceedings. *Vet Infect Dis Org* 1983;346–364.
11. White D G, Andrews A H. Adequate concentration of circulating colostral proteins for market calves. *Vet Rec* 1986;119:112–113.
12. Selim S A, Smith B P, Cullor J S, Et al. Serum immunoglobulins in calves: their effects and two easy, reliable means of measurement. *Vet Med* 1995;90:387–404.
13. Butler J E. Bovine immunoglobulins: a review. *J Dairy Science,* 1969;52, 1895.
14. Mach J P, Pahud J J, Isliker H. IgA with 'Secretory piece' in bovine colostrum and saliva. *Nature,* 1969;223,952.
15. Hammer D K, Kickhofen B, Schmid T. Detection of homocytotropic antibody associated with a unique immunoglobulin class in the bovine species. *Europ. J. Immunol.,* 1971;1,249.
16. Wells P W, Eyre P. Bovine homocytotropic (skin sensitizing) antibody. *Immunol. Commun.,* 1972;1,105.
17. Nielsen K, Holmes W, Wilkie B, Tizard I. Bovine reagenic antibody. I. Rat mast cell degranulation by bovine allergic serum. *Int. Archs Allergy appl. Immunol.,* 1976;51,441.
18. Babel C L, Lang R W. Identification of a new immunoglobulin subclass in three ruminant species. *Fed. Proc.,* 1976;35,272.
19. Osburn B I. The ontogeny of the ruminant immune system and its significance in the understanding of maternal-fetal-neonatal relationships. J E Butler(Ed). *The ruminant immune system,* 1981, pp 91–103. Plenum Press, New York, N.Y.
20. Etzel L R, Strohbehn R E, McVicker J K. Development of an automated turbidimetric immunoassay for quantification of bovine serum immunoglobulin G. *Am. J. Vet. Res.,* 1997; 58, 1201.
21. Bogin E, Avidar Y, Shenkler S. A rapid field test for the determination of colostral ingestion by calves, based on γ-glutamyltransferase. *Eur. J. Clin. Chem. Biochem.* 1993;31,695.

What is claimed is:

1. A method of determining if the concentration of IgG antibodies in biological fluids of a neonatal bovine is below a predetermined threshold level, the method comprising the steps of:

taking a sample of the biological fluid from the neonatal bovine;

exposing a quantity of the sample to a quantity of dehydrated IgG complexing agent coupled with a labeling agent that is immobilized at a sample position on a protein binding membrane to yield a conjugate;

exposing the conjugate to a quantity of dehydrated standard bovine IgG immobilized at a test position on the membrane, the test position being spaced from the sample position on the membrane; and observing binding of the IgG complexing agent with the standard bovine IgG evidenced by a color change from the labeling agent at the test position, which color change indicates that the concentration of IgG antibodies is below the predetermined threshold level.

2. The method of claim 1, further including the steps of:

exposing the conjugate to a quantity of dehydrated anti-IgG complexing agent immobilized at a control position on the membrane, the control position being spaced from the test position; and observing interaction of the IgG complexing agent and the anit-IgG complexing agent evidenced by a color change from the labeling agent at the control position.

3. The method of claim 1 wherein the predetermined threshold level is about 10 mg/ml.

4. The method of claim 1 wherein the predetermined threshold level is about 10 mg/ml.

5. The method of claim 1 wherein the labeling agent is selected from the group consisting of collodial gold and latex particles.

6. The method of claim 2 wherein the labeling agent is selected from the group consisting of collodial gold and latex particles.

7. The method of claim 3 wherein the labeling agent is selected from the group consisting of collodial gold and latex particles.

8. The method of claim 4 wherein the labeling agent is selected from the group consisting of collodial gold and latex particles.

* * * * *

UNITED STATES PATENT AND TRADEMARK OFFICE
CERTIFICATE OF CORRECTION

PATENT NO. : 6,245,577 B1  
DATED : June 12, 2001  
INVENTOR(S) : Jerry K. McVicker et al.

Page 1 of 1

It is certified that error appears in the above-identified patent and that said Letters Patent is hereby corrected as shown below:

<u>Column 9,</u>  
Line 1, delete "1" and substitute -- 2 -- therefor.

Signed and Sealed this

Fourteenth Day of May, 2002

*Attest:*

JAMES E. ROGAN  
*Attesting Officer*   *Director of the United States Patent and Trademark Office*